(12) United States Patent
Yoshida

(10) Patent No.: US 7,514,685 B2
(45) Date of Patent: Apr. 7, 2009

(54) INFRARED-TYPE GAS DETECTOR

(75) Inventor: Takahiko Yoshida, Okazaki (JP)

(73) Assignee: DENSO CORPORATION, Kariya (JP)

( * ) Notice: Subject to any disclaimer, the term of this patent is extended or adjusted under 35 U.S.C. 154(b) by 22 days.

(21) Appl. No.: 11/898,228

(22) Filed: Sep. 11, 2007

(65) Prior Publication Data

US 2008/0062426 A1    Mar. 13, 2008

(30) Foreign Application Priority Data

Sep. 12, 2006    (JP) ............... 2006-247124

(51) Int. Cl.
*G01N 21/00* (2006.01)
(52) U.S. Cl. .................................. 250/338.5
(58) Field of Classification Search .... 250/338.1–338.5
See application file for complete search history.

(56) References Cited

U.S. PATENT DOCUMENTS 5,561,523 A    10/1996    Blomberg et al.
6,590,710 B2    7/2003    Hara et al.
2003/0116711 A1    6/2003    Hara et al.
2004/0196874 A1*    10/2004    Spiegelberg et al. ........... 372/6

FOREIGN PATENT DOCUMENTS

JP    A-11-142245    5/1999

* cited by examiner

*Primary Examiner*—David P Porta
*Assistant Examiner*—Kiho Kim
(74) *Attorney, Agent, or Firm*—Posz Law Group, PLC

(57) ABSTRACT

An infrared-type gas detector is provided with a Fabry-Perot filter through which infrared having a predetermined wavelength is selected to pass, a first detection unit for receiving the infrared having passed through the Fabry-Perot filter and outputting a detection signal corresponding to an absorption amount of the infrared, and a case member having a window portion through which the infrared passes and housing therein the first detection unit and the Fabry-Perot filter in an inner space of the case member. The case member has at least one ventilation portion through which the inner space of the case member is communicated with the exterior of the case member.

19 Claims, 5 Drawing Sheets

INFRARED-TYPE GAS DETECTOR

CROSS REFERENCE TO RELATED APPLICATION

This application is based on a Japanese Patent Application No. 2006-247124 filed on Sep. 12, 2006, the disclosure of which is incorporated herein by reference.

FIELD OF THE INVENTION

The present invention relates to an infrared-type gas detector.

BACKGROUND OF THE INVENTION

Generally, an infrared-type gas detector is provided to detect a concentration of a detected gas according to an absorption amount of infrared which has a particular wavelength and absorbed by the detected gas. For example, with reference to JP-7-286809A and JP-2001-228326A, the infrared-type gas detector is provided with a Fabry-Perot filter.

The Fabry-Perot filter has a fixed mirror and a moving mirror which faces the fixed mirror and is separated from the moving mirror with a predetermined gap. A predetermined voltage is applied between a fixed electrode arranged at the fixed mirror and a movable electrode arranged at the moving mirror, so that the moving mirror is displaced. Thus, the infrared having a desirable wavelength corresponding to the gap which varies in response to the displacement of the moving mirror can be selected to pass. Therefore, the infrared-type gas detector having the Fabry-Perot filter can detect the infrared having multiple wavelength fields by a single infrared receiving element.

Moreover, as disclosed in JP-11-142245A, an infrared-type gas detector is provided with a Fabry-Perot filter and an infrared receiving element which are packaged in an inner space of a can. The inner space is hermetically closed.

However, in the case where the Fabry-Perot filter and the infrared receiving element are can-packaged, the pressure of the inner space will increase due to the increase of the temperature of the inner space because of the heating of the can package due to the infrared or the heat generation of a driving element (for driving Fabry-Perot filter, for example) arranged in the inner space. That is, unevenness will occur in the gap of the Fabry-Perot filter due to the variation (that is, variation of resistance due to gas) in the pressure of the inner space, even when the applied voltage is same.

SUMMARY OF THE INVENTION

In view of the above-described disadvantage, it is an object of the present invention to provide an infrared-type gas detector where unevenness in a gap of a Fabry-Perot filter is reduced.

According to a first aspect of the present invention, an infrared-type gas detector is provided with a Fabry-Perot filter through which infrared having a predetermined wavelength is selected to pass, a first detection unit for receiving the infrared having passed through the Fabry-Perot filter and outputting a detection signal corresponding to an absorption amount of the infrared, and a case member having a window portion through which the infrared passes and housing therein the first detection unit and the Fabry-Perot filter in an inner space of the case member. The case member has at least one ventilation portion through which the inner space of the case member is communicated with the exterior of the case member.

Because the ventilation portion constructs a passage for communicating the interior of the case member and the exterior thereof, the pressure variation of the inner space due to the temperature variation thereof can be lowered. Thus, the unevenness of the gap of the Fabry-Perot filter can be restricted.

According to a second aspect of the present invention, an infrared-type gas detector is provided with a Fabry-Perot filter through which infrared having a predetermined wavelength is selected to pass, a first detection unit for receiving the infrared having passed through the Fabry-Perot filter and outputting a detection signal corresponding to an absorption amount of the infrared, and a case member having a window portion through which the infrared passes and defining therein an inner space which is substantially hermetically sealed and in which the first detection unit and the Fabry-Perot filter are housed. The inner space of the case member is in a pressure-reducing state as compared with an atmospheric pressure.

Because the inner space of the case member is set in the pressure-reducing state as compared with the atmospheric pressure, the pressure variation of the inner space due to the temperature variation thereof can be lowered. Thus, the unevenness of the gap of the Fabry-Perot filter can be restricted.

According to a third aspect of the present invention, an infrared-type gas detector is provided with a Fabry-Perot filter having a fixed mirror and a moving mirror which faces the fixed mirror and spaced from the fixed mirror at a predetermined gap, a first detection unit for receiving the infrared having passed through the Fabry-Perot filter and outputting a detection signal corresponding to an absorption amount of the infrared, a case member having a window portion through which the infrared passes and defining therein an inner space which is substantially hermetically sealed and in which the first detection unit and the Fabry-Perot filter are housed, a second detection unit which is housed in the case member to detect at least one of a temperature and a pressure of the inner space of the case member, and a control unit. A predetermined voltage is applied between a fixed electrode arranged at the fixed mirror and a moving electrode arranged at the moving mirror to displace the moving mirror, so that the gap is changed and infrared having a predetermined wavelength corresponding the gap is selected to pass the Fabry-Perot filter. The control unit corrects and controls the voltage applied between the fixed electrode and the moving electrode based on a detection result of the second detection unit.

In this case, at lease one of the temperature variation of the inner space and the pressure variation thereof due to the temperature variation which cause the unevenness of the gap of the Fabry-Perot filter can be detected. Furthermore, the control unit can correct and control the voltage applied between the fixed electrode and the moving electrode based on the detection result of the second detection unit, so that the gap of the Fabry-Perot filter keeps constant to be unrelated to the temperature variation (pressure variation) of the inner space. Thus, the unevenness of the gap of the Fabry-Perot filter can be restricted.

BRIEF DESCRIPTION OF THE DRAWINGS

Other objects, features and advantages of the present invention will become more apparent from the following detailed description made with reference to the accompanying drawings, in which.

DETAILED DESCRIPTION OF THE EXAMPLED EMBODIMENTS

First Embodiment

Figure 1:
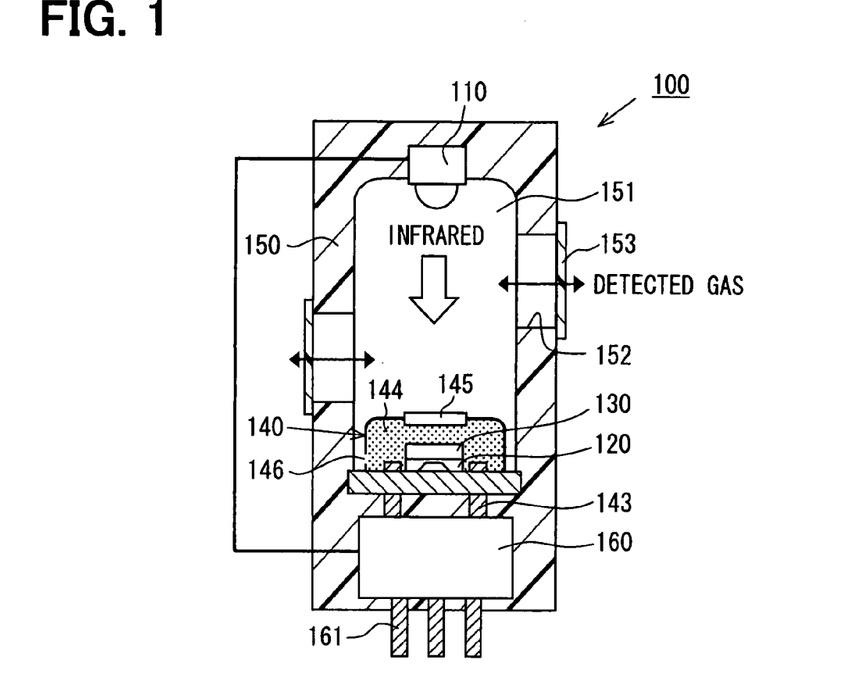
FIG. 1 is a schematic sectional view showing an infrared-type gas detector according to a first embodiment of the present disclosure.

An infrared-type gas detector 100 according to a first embodiment of the present invention will be described with reference to FIGS. 1-5. As shown in FIG. 1, the infrared-type gas detector 100 has a light source 110 for radiating infrared, a first detection unit 120 for detecting infrared, a Fabry-Perot filter 130 which is arranged at a light path of the infrared from the light source 110 to the first detection unit 120 and through which the infrared having a predetermined wavelength passes (that is, infrared selectively passes Fabry-Perot filter 130), a can package member 140 (case member) in which the first detection unit 120 and the Fabry-Perot filter 130 are housed, and a housing 150 in which the light source 110, the first detection unit 120, the Fabry-Perot filter 130 and the case member 140 are accommodated.

The light source 110 can be constructed of any source which radiates the infrared having a predetermined wavelength field. For example, the light source 110 can be constructed of an incandescent lamp, or a membrane which is used as a thin-walled portion arranged at a base plate and at which a resistance is formed, or the like. In this embodiment, the incandescent lamp which radiates the infrared including the wavelength field from about 2 μm to about 10 μm is used as the light source 110.

The first detection unit 120 can be constructed of a member (light-receiving element) which receives the infrared and outputs detection signals in response to an absorption amount (intensity) of the infrared. Specifically, the first detection unit 120 can be constructed of a detection element of a thermopile type having a thermocouple, or a detection element of a bolometer type having a resistor, or a detection element of a pyroelectric type having a pyroelectric material, or the like. In this embodiment, the first detection unit 120 is constructed of the detection element of the thermopile type having the thermocouple.

Figure 2:
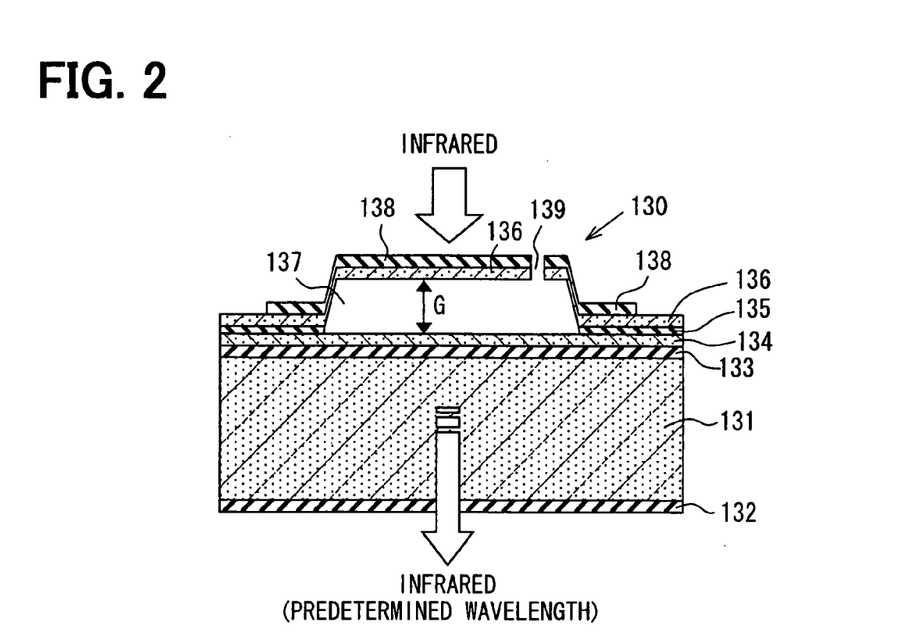
FIG. 2 is a schematic sectional view showing a Fabry-Perot filter of the infrared-type gas detector according to the first embodiment.

The Fabry-Perot filter 130 is a wavelength selective filter of a variable type, and can have a well-known construction. Specifically, as shown in FIG. 2, the Fabry-Perot filter 130 has a board 131, a fixed mirror 134 arranged at the board 131, and a moving mirror 136 which faces the fixed mirror 134 and is distanced from the fixed mirror 134 with a predetermined gap G therebetween.

The board 131 can be a semiconductor board made of silicon, and provided with a reflection-restricting film 132 (e.g., oxidation silicon film) at a first surface (e.g., surface of lower side shown in FIG. 2) of the board 131. An insulating film 133 (e.g., oxidation silicon film) is arranged at a second surface (e.g., surface of upper side shown in FIG. 2) of the board 131. The first surface and the second surface are respectively positioned at the opposite sides of the board 131. The insulating film 133 has the effect of a reflection-restricting film, and insulates the fixed mirror 134 from the board 131.

The fixed mirror 134, being constructed of a polycrystalline silicon film, is arranged at the upper surface of the insulating film 133 which is positioned at the upper side of the board 131. The fixed mirror 134 has a pad portion (not shown) as an electrode which is positioned at the end portion of the fixed mirror 134 and in which impurity having a high concentration is infused.

An oxidation silicon film 135 is arranged at the upper surface of the fixed mirror 134. A part of the oxidation silicon film 135 is eliminated by etching or the like. The moving mirror 136, being constructed of a polycrystalline silicon film, is formed at field of the oxidation silicon film 135 and at the field where the oxidation silicon film 135 is eliminated.

A nitride silicon film 138 is arranged at the upper surface of the moving mirror 136, and used as a mask for forming a cavity portion 137. The cavity portion 137 includes the elimination field of the oxidation silicon film 135.

The moving mirror 136 is disposed opposite to the fixed mirror 134 with the cavity portion 137 being arranged therebetween. The moving mirror 136 positioned at the upper portion of the cavity portion 137 is constructed to be displaceable (deformable) with respect to the fixed mirror 134 when a voltage is applied.

The moving mirror 136 has a pad portion (not shown) as an electrode which is positioned at the end portion of the moving mirror 136 and in which impurity having a high concentration is infused. An etching hole 139 is formed at the nitride silicon film 138 and the moving mirror 136, and penetrates the nitride silicon film 138 and the moving mirror 136.

When the predetermined voltage is applied between the pad portion arranged at the fixed mirror 134 and that arranged at the moving mirror 136, an electrostatic attractive force occurs between the fixed mirror 134 and the moving mirror 136 so that the moving mirror 136 at the cavity portion 137 has a displacement with respect to the fixed mirror 134.

Thus, the infrared (having specific wavelength) passing due to interference is selected in response to the distance (gap G of the cavity portion 137) between the fixed mirror 134 and the moving mirror 136. Specifically, the infrared having the wavelength λ which is twice as long as the gap G of the cavity portion 137 is selectively made pass.

In this embodiment, for the sake of detection of the concentration of detected gas (e.g., $CO_2$), the gap G (of the cavity portion 137) before the moving mirror 136 has a displacement (that is, gap G of initial state) is set to be substantially equal to about ½ of the specific wavelength λ so that the infrared having the specific wavelength λ (for example, central wavelength is about 4.26 μm) can pass through the Fabry-Perot filter 130. Thus, by changing the gap G, the infrared having a wavelength (for example, 4 μm) other than the specific wavelength λ can be detected as a reference.

Figure 3:
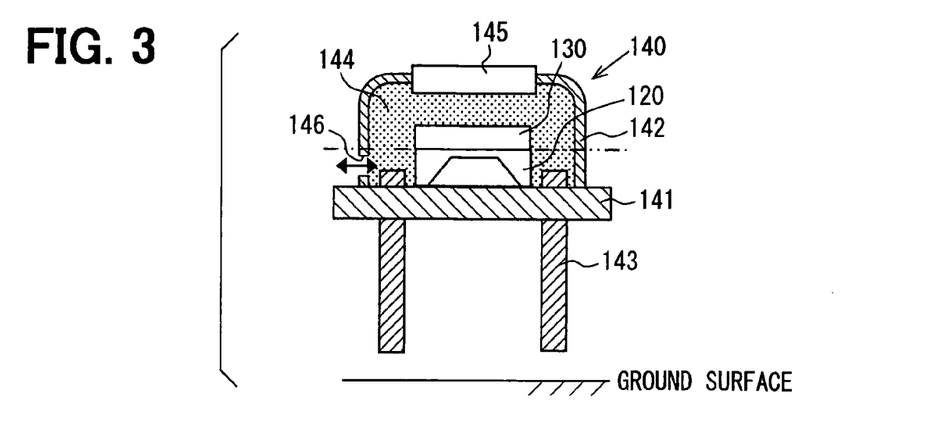
FIG. 3 is a schematic sectional view showing a case member of the infrared-type gas detector according to the first embodiment.

As shown in FIG. 3, the case member 140 houses the first detection unit 120 and the Fabry-Perot filter 130 in the inner space 144 thereof, to protect the first detection unit 120 and the Fabry-Perot filter 130. The case member 140 has a cap portion 142 and a pedestal portion 141 which can be made of a metal (e.g., iron), for example. The detection axis of the first detection unit 120 can be arranged to be substantially perpendicular to the ground surface.

The first detection unit 120, being constructed of a sensor chip, is fixed (by adhering, for example) at the pedestal portion 141, in such a manner that a back surface (which is opposite to light-receiving surface of infrared of first detection unit 120) of the first detection unit 120 faces the pedestal portion 141. The Fabry-Perot filter 130 is stacked at the first detection unit 120, for example, by adhering, to be fixed thereto.

Terminals 143 penetrate the pedestal portion 141 in a substantially up-down direction, through the penetration portions of the pedestal portion 141. The penetration portions are hermetically sealed. The terminal 143 is electrically connected with the first detection unit 120 and the electrode of the Fabry-Perot filter 130, by bonding wires (not shown). In this state, the cap portion 142 is assembled with the pedestal portion 141 by welding, or adhering or the like, in such a manner that the first detection unit 120 and the Fabry-Perot filter 130 are housed in the inner space 144 defined between the cap portion 142 and the pedestal portion 141. Moreover, gas such as air (which is named as filling gas to be distinguished from detected gas) is filled in the inner space 144.

The cap portion 142 has a cylinder shape, for example. The cap portion 142 is bottomed and provided with a window portion 145 through which the infrared passes. The window portion 145 is arranged at the upper wall (that is, bottom of cap portion 142 which faces the pedestal portion 141) of the cap portion 142, and positioned corresponding to the first detection unit 120.

The cap portion 142 is further provided with a through hole 146 (ventilation portion) which can be arranged at a side wall (which surrounds the bottom) of the cap portion 142, as a ventilation passage of the filling gas between the inner space 144 of the case member 140 and the exterior of the case member 140. The size, arrangement, and number of the through holes 146 are not limited.

In this embodiment, for example, the cap portion 142 can be provided with the single through hole 146, which is arranged at the lower side than the lowermost portion (indicated by chain double-dashed line in FIG. 3) of the Fabry-Perot filter 130 in the direction (up-down direction) vertical to the ground surface.

Thus, even when the foreign matter intrudes upon the inner space 144 of the case member 140 through the through hole 146 (ventilation portion), the Fabry-Perot filter 130 can be restricted from malfunctioning due to foreign matter. It is desirable for the through hole 146 to be arranged at the lower side than the Fabry-Perot filter 130 in the gravity direction. That is, in the case where the infrared-type gas detector 100 is mounted to a vehicle, the through hole 146 is positioned at the lower side than the Fabry-Perot filter 130 even when the vehicle is in an inclined state (for example, when the vehicle climbs a gradient). Thus, the Fabry-Perot filter 130 can be restricted from malfunctioning due to foreign matter.

The housing 150 holds therein the light source 110, the first detection unit 120, the Fabry-Perot filter 130 and the case member 140 which are arranged at the predetermined positions, and protect the light source 110, the first detection unit 120, the Fabry-Perot filter 130 and the case member 140.

As shown in FIG. 1, the housing 150 can have a cylinder shape having the two ends of the longitudinal direction which are closed. The light source 110 is arranged in the inner space 151 of the housing 150, and positioned at the one end of the housing 150. The first detection unit 120 is arranged in the inner space 151, and positioned at the other end (facing the one end) of the housing 150.

The housing 150 is provided with an intake hole 152 through which detected gas (for example, $CO_2$) can be introduced into the inner space 151 (in which detection system including light source 110, first detection unit 120 and Fabry-Perot filter 130 are arranged) of the housing 150. The intake hole 152 is covered by a dustproof film 153 (dustproof filter) for restricting foreign matter such as rubbish and the like intruding upon the inner space 151. The dustproof film 153 is constructed such that the detected gas can pass through the dustproof film 153 while the foreign matter is restricted from passing.

The infrared-type gas detector 100 has a circuit chip 160. The circuit chip 160 includes a power source for supplying power to the light source 110 and the Fabry-Perot filter 130, a control unit for controlling the energization state, a processing unit for processing (e.g., amplifying) the detection signals from the first detection unit 120, a calculating unit for calculating the concentration of the detected gas based on the detection signals, and the like.

The circuit chip 160 is fixed to the housing 150, and electrically connected with the first detection unit 120 and the Fabry-Perot filter 130, through the terminal 143. Moreover, the circuit chip 160 is electrically connected with the light source 110. In this embodiment, the circuit chip 160 is electrically connected with output terminals 161, and constructed to output the calculation result to the exterior through the output terminals 161.

When the light source 110 is supplied with power in response to a signal from the circuit chip 160, the infrared having a predetermined wavelength field is radiated from the light source 110 toward the side of the first detection unit 120 in the direction indicated by the hollow arrow in FIG. 1.

In this case, when the detected gas which is the detection object is introduced into the inner space 151 of the housing 150 through the intake hole 152, the part of the radiated infrared which has the specific wavelength (absorption wavelength of detected gas) is absorbed by the detected gas when the infrared passes the detected gas.

At a detection mode of the infrared-type gas detector 100, when the infrared including the specific wavelength reaches the Fabry-Perot filter 130 through the window portion 145 of the case member 140, only the infrared having the specific wavelength can pass through the Fabry-Perot filter 130 to be received by the first detection unit 120.

In this case, because the intensity of the infrared having the specific wavelength having reached the first detection unit 120 varies in response to the concentration of the detected gas, the output of the first detection unit 120 accordingly varies. Thus, based on the detection signal of the first detection unit 120, the concentration of the detected gas can be measured based on the detection signals of the first detection unit 120.

In this embodiment, in addition to the detection mode, a reference mode is provided for the infrared-type gas detector 100 to detect the infrared (as reference) having the wavelength other than the wavelength of the detected gas, to restrict the temperature dependency of the infrared absorption amount of the detected gas and the affection of the variation in the infrared amount due to the deterioration of the light source 110. Specifically, by the signal from the circuit chip 160, the detection mode can be switched into the reference mode where the gap G of the Fabry-Perot filter 130 can be changed into the gap corresponding to the infrared wavelength of the reference.

According to this embodiment, the through hole 146 is arranged to communicate the inner space 144 of the case member 140 with the exterior of the case member 140. Therefore, even when the temperature of the inner space 144 increases due to a heating of the case member 140 by the infrared or the like, air (filling gas) in the inner space 144 which expands can escape to the exterior of the inner space 144. That is, the pressure variation of the inner space 144 due to the temperature variation can be lowered. That is, the pressure variation of the inner space 144 can be restricted.

Because the filling gas in the inner space 144 constructs a resistance against the displacement of the moving mirror 136, unevenness in the gap G of the Fabry-Perot filter 130 may occur even when the applied voltage is same, if the pressure of the inner space 144 varies. According to this embodiment, the unevenness due to the resistance of the pressure of the gas when the moving mirror 136 has a displacement can be lowered or prevented as compared with the conventional device. Therefore, the unevenness of the gap G of the Fabry-Perot filter 130 can be restricted.

In this embodiment, the infrared-type gas detector 100 is provided with the light source 110, the first detection unit 120, the Fabry-Perot filter 130, the case member 140 and the housing 150. In this case, the light source 110, the first detection unit 120 and the Fabry-Perot filter 130 can be fixed to the housing 150, with being disposed at desirable positions. Moreover, because the first detection unit 120 and the Fabry-Perot filter 130 are housed in the inner space 144 of the case member 140, the workability of the arrangement at the housing 150 can be improved. For example, the wire break can be restricted.

Alternatively, the infrared-type gas detector 100 can be also provided with at least the first detection unit 120, the Fabry-Perot filter 130, and the case member 140 where the first detection unit 120 and the Fabry-Perot filter 130 are housed. In this case, the concentration of the detected gas can be measured if the infrared can be received.

According to this embodiment, the concentrations of the multiple kinds of the detected gas can be also respectively measured, by changing the voltage applied to the Fabry-Perot filter 130.

Figure 4:
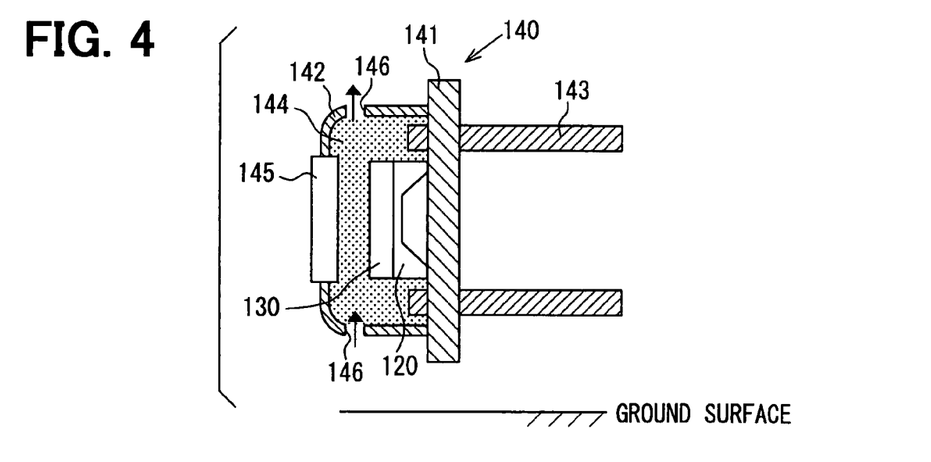
FIG. 4 is a schematic sectional view showing a case member according to a first modification example of the first embodiment.

Furthermore, as described above, an example that the through hole 146 is arranged at the lower side than the Fabry-Perot filter 130 in the vertical direction with respect to the ground surface is provided. However, according to a first modification example of this embodiment, as shown in FIG. 4, the through hole 146 can be also arranged at the top of the cap portion 142 in the vertical direction with respect to the ground surface. In this case, the detection axis of the first detection unit 120 is arranged to be substantially parallel to the ground surface, and the through hole 146 is arranged at the side wall of the cap portion 142.

In this case, the heated gas which is filled in the inner space 144 readily escapes to the exterior through the through hole 146, as compared with the construction where the through hole 146 is arranged at the lower side than the Fabry-Perot filter 130.

In contrast, in the example where the detection axis of the first detection unit 120 is arranged to be substantially vertical to the ground surface as shown in FIG. 3, the same effect can be provided if the through hole 146 is arranged with the forming surface of the window portion 145 being disposed as the upper surface.

As shown in FIG. 4, the multiple through holes 146 can be also arranged at the case member 140 in such a manner that the through holes 146 are separated from each other. Thus, the inner space 144 and the exterior of the case member 140 can be more substantially communicated, as compared with the construction where the one through hole 146 is arranged at the case member 140. Thus, the unevenness of the gap G of the Fabry-Perot filter 130 can be lowered. In the construction shown in FIG. 4, the through holes 146 are respectively arranged at the side wall (of the cap portion 142) which is positioned at the upper side and the side wall (of the cap portion 142) which is positioned at the lower side. The two through holes 146 face each other. Thus, the filling gas can flow in the substantially vertical direction with respect to the ground surface, so that the filling gas can outflow and inflow efficiently with respect to the inner space 144.

Moreover, in this embodiment, the through hole 146 as the ventilation portion is formed at the cap portion 142 of the case member 140. Alternatively, the ventilation portion can be also constructed of a part of the case member 140 through which the interior of the case member 140 and the exterior of the case member 140 can be communicated with each other.

Figure 5:
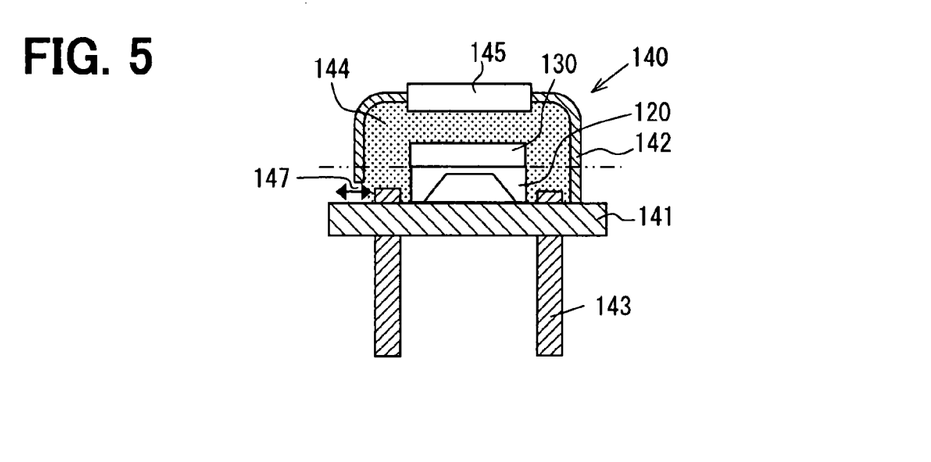
FIG. 5 is a schematic sectional view showing a case member according to a second modification example of the first embodiment.

For example, according to a second modification example of the first embodiment, as shown in FIG. 5, the ventilation portion can be constructed of a gap 147 arranged between the surface of the pedestal portion 141 and the surface of the cap portion 142 which face each other. More alternatively, the cap portion 142 can be also provided with both the through hole 146 and the gap 147. The contact area between the pedestal portion 141 and the cap portion 142 in the construction where the through hole 146 is provided is larger than that in the construction where the gap 147 is provided. Moreover, in the case where the light source 110 is not integrated, the ventilation portion can be also arranged at the pedestal portion 141. For example, the ventilation portion can be constructed of a through hole which is formed at the pedestal portion through which the interior of the case member 140 and the exterior of the case member 140 can be communicated with each other. Alternatively, the ventilation portion can be also constructed of a recess which is formed at the pedestal portion and includes a part positioned in the inner space 144 and a part positioned outside of the inner space 144, so that the interior of the cap portion 142 and the exterior thereof can be communicated with each other.

Moreover, the ventilation portion can be also covered by a filter through which gas can pass and by which the intrusion of foreign matter can be restricted. That is, this filter is breathing and dustproof. Alternatively, the through hole 146 can be also provided with a porous shape. Thus, no matter where the ventilation portion is arranged and no matter whether or not the housing 150 having the dustproof film 153 is provided, the damage of the Fabry-Perot filter 130 due to the foreign matter can be restricted.

Second Embodiment

A second embodiment of the present invention is described with reference to FIG. 6.

In the above-described first embodiment, the ventilation portion (for example, through hole 146 and gap 147) is arranged at the case member 140 where the first detection unit 120 and the Fabry-Perot filter 130 are housed, to restrict the unevenness of the gap G of the Fabry-Perot filter 130. According to the second embodiment, as shown in FIG. 6, the inner space 144 of the case member 140 is substantially hermetically sealed and set at a pressure-reducing state (e.g., vacuum state) as compared with the atmosphere.

According to the second embodiment, because the inner space 144 of the case member 140 is in the decompression state (attenuated state) as compared with the atmosphere, the pressure variation (unevenness of resistance due to gas) of the inner space 144 in response to the temperature variation can be reduced as compared with the conventional device where the pressure in the inner space 144 is substantially equal to the atmospheric pressure. Thus, the unevenness of the gap G of the Fabry-Perot filter 130 can be reduced. In the case where the inner space 144 is provided with the vacuum state, the resistance due to the filling gas can be restricted so that the unevenness of the gap G of the Fabry-Perot filter 130 can be prevented.

Alternatively, the inner space 144 can be also filled with gas (filling gas) having a lower viscosity than air. It is desirable that the inner space 144 is filled with hydrogen gas or helium gas to have the decompression state. In this case, the resistance of the filling gas when the moving mirror 136 has a displacement can be reduced as compared with the decompression state due to air. Therefore, the unevenness of the gap G of the Fabry-Perot filter 130 can be further reduced.

Figure 6:
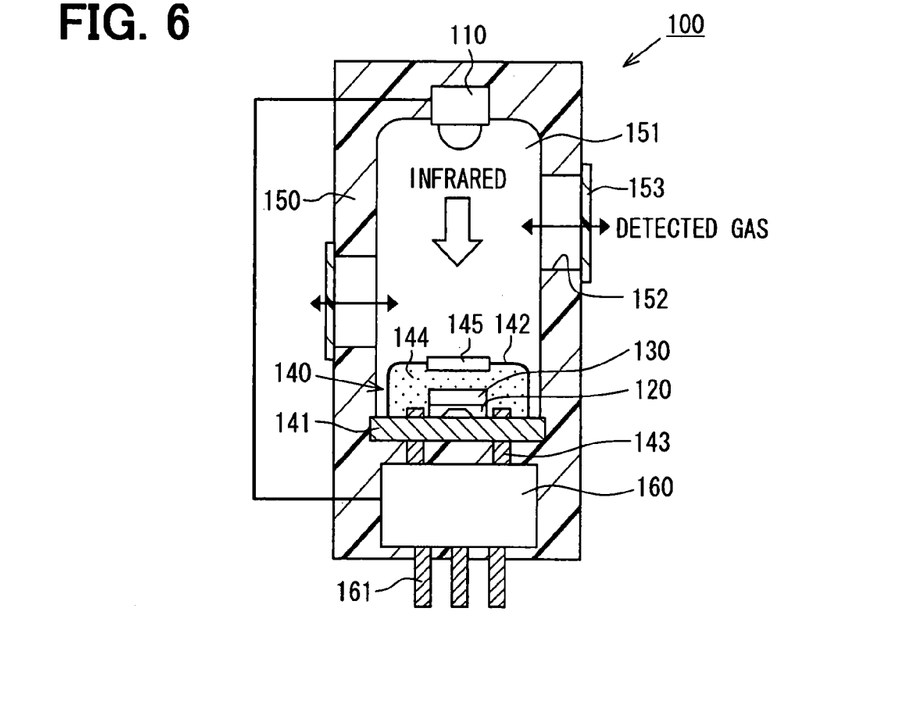
FIG. 6 is a schematic sectional view showing an infrared-type gas detector according to a second embodiment of the present disclosure.

As shown in FIG. 6, the infrared-type gas detector 100 can be provided with the light source 110, the first detection unit 120, the Fabry-Perot filter 130, the case member 140 and the housing 150. However, the infrared-type gas detector 100 can be also provided with at least the first detection unit 120, the Fabry-Perot filter 130, and the case member 140 in which the first detection unit 120 and the Fabry-Perot filter 130 are housed.

About the infrared-type gas detector 100, what has not described in the second embodiment is the same with the first embodiment.

Third Embodiment

A third embodiment of the present invention is described with reference to FIG. 7.

According to the above-described second embodiment, the inner space 144 is provided with the decompression state (pressure-reducing state) as compared with the atmosphere to reduce the unevenness of the gap G of the Fabry-Perot filter 130. In contrast, according to the third embodiment, the pressure state of the inner space 144 is not specially limited, while a second detection unit 170 is arranged in the inner space 144 of the case member 140 to detect at least one of the temperature and the pressure in the inner space 144. Based on the detection result of the detection unit, the control unit (correction control unit) of the circuit chip 160 can correct and control the voltage applied to the Fabry-Perot filter 130.

Figure 7:
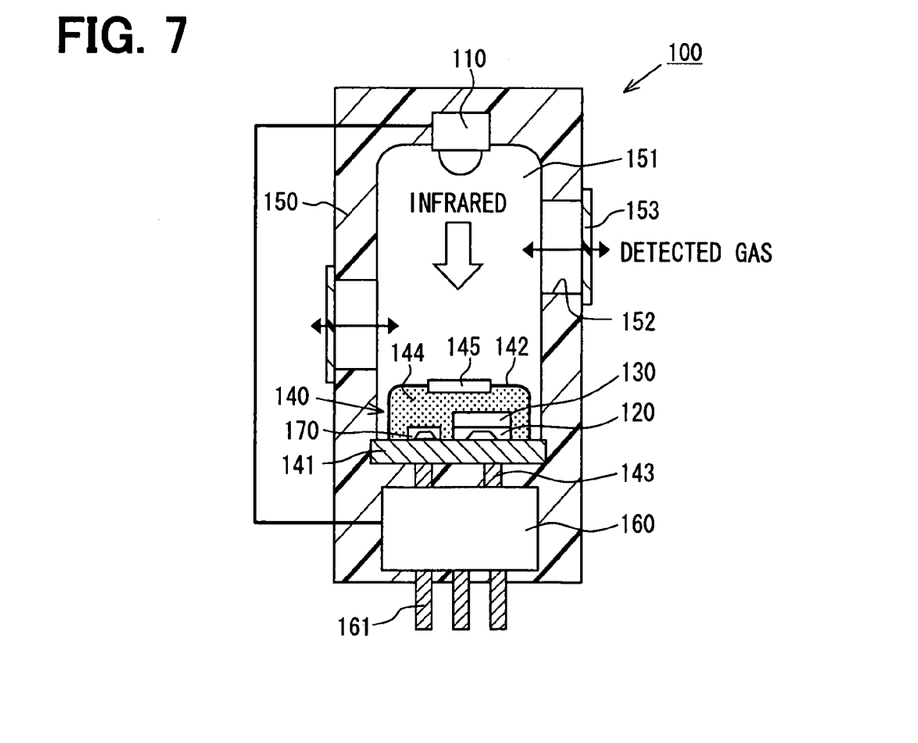
FIG. 7 is a schematic sectional view showing an infrared-type gas detector according to a third embodiment of the present disclosure.

As shown in FIG. 7, the second detection unit 170 (e.g., pressure sensor) is arranged in the inner space 144 of the case member 140. The second detection unit 170 is constructed to detect the pressure variation of the inner space 144 which is caused due to the temperature variation. For example, the second detection unit 170 can be constructed of a pressure sensor of a semiconductor type having a board with a thin-walled portion where a distortion gauge is formed.

The second detection unit 170 is fixed (by adhering, for example) to the pedestal portion 141, in such a manner that the back surface (which is opposite to the forming surface of the distortion gauge) of the second detection unit 170 faces the pedestal portion 141.

The second detection unit 170 is electrically connected with the terminal 143 through a bonding wire (not shown). A storage unit such as a memory is arranged at the circuit chip 160 which is electrically connected with the second detection unit 170 through the terminal 143. The corresponding relation among the voltage applied to the Fabry-Perot filter 130, the pressure of the inner space 144 and the gap G of the Fabry-Perot filter 130 is beforehand memorized in the storage unit.

The correction control unit is provided to output a signal for correcting the voltage applied to the control unit for controlling the energization state to keep the gap G of the Fabry-Perot filter 130 constant, based on the detection signal of the second detection unit 170 and the corresponding relation memorized in the memory.

For example, according to the conventional device, because the applied voltage is same even when the pressure of the inner space 144 increases in response to the increase of the temperature, the displacement of the moving mirror 136 reduces and the gap G becomes larger than the desirable value. In contrast, according to this embodiment, the variation of the pressure of the inner space 144 can be caught based on the detection signal of the second detection unit 170, and the applied voltage which is higher than that before the pressure increase can be supplied for the Fabry-Perot filter 130 so that the gap G has the desirable value under this pressure of the inner space 144.

According to this embodiment, the second detection unit 170 can detect the pressure variation in response to the temperature variation of the inner space 144. Moreover, based on the detection signal of the second detection unit 170, the circuit chip 160 having the correction control unit can correct and control the applied voltage so that the gap G of the Fabry-Perot filter 130 can become substantially constant without being affected by the pressure variation (temperature variation) of the inner space 144. Therefore, the unevenness of the gap G of the Fabry-Perot filter 130 can be reduced.

The first detection unit 120 and the second detection unit 170 can be respectively arranged at different boards. Alternatively, the first detection unit 120 and the second detection unit 170 can be also arranged at a same board, so that the infrared-type gas detector 100 can be small-sized.

Figure 8A:
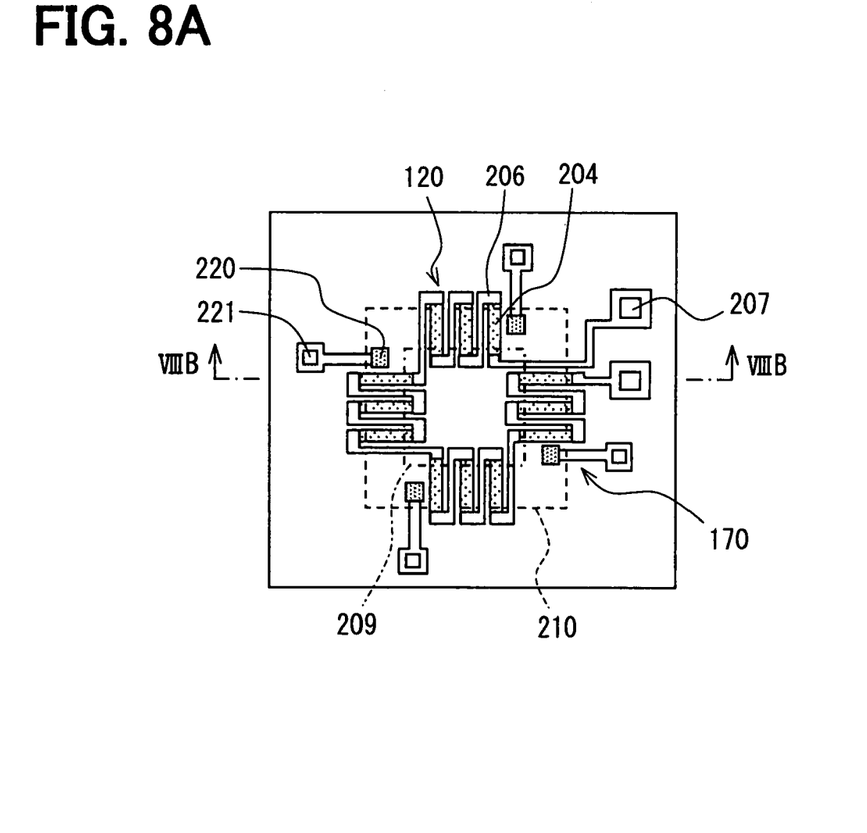
FIG. 8A is a schematic plan view showing an infrared-type gas detector according to a first modification example of the third embodiment.
Figure 8B:
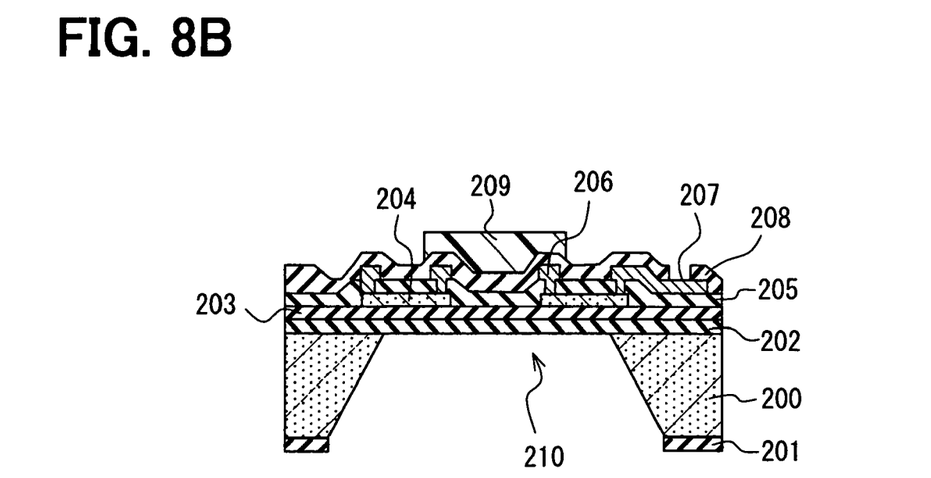
FIG. 8B is a schematic sectional view taken along the line VIIIB-VIIIB in FIG. 8A.

For example, according to a first modification example of this embodiment, as shown in FIGS. 8A and 8B, it is desirable that a board 200 where a membrane 210 as a thin-walled portion is arranged is provided and the first detection unit 120 and the second detection unit 170 (for detecting the pressure of the inner space 144) are arranged at the membrane 210. Thus, the infrared-type gas detector 100 can be further small-sized.

The first detection unit 120 (of thermopile type, for example) can be constructed of thermocouples each of which includes a wiring 206 and the polycrystalline silicon film 204. That is, as shown in FIG. 8A, the multiple polycrystalline silicon films 204 and the multiple wirings 206 (which are made of different material from that of the polycrystalline silicon film 204) are alternately arranged in series to construct a thermopile. Each of joining portions includes a warm contact portion formed at the membrane 210 having a small heat capacity, and a cold contact portion formed at the board 200 which has a large heat capacity and is positioned at the outer side of the membrane 210.

In this case, the board 200 can be made of silicon. A nitride silicon film 201 as a mask is arranged at the lower surface of the board 200. An insulating film 202 (e.g., nitride silicon film) as an etching stopper is arranged at the upper surface of the board 200. An oxidation silicon film 203 is arranged on the insulating film 202.

The polycrystalline silicon films 204 are disposed on the oxidation silicon film 203. Each of the polycrystalline silicon films 204 is positioned to cover a part of the membrane 210 and a part of the thick-walled portion of the board 200. The polycrystalline silicon film 204 is connected with the wiring 206 (which is made of aluminum, for example) through an interlayer insulating film 205 (e.g., BPSG). The wiring 206 connects the end portions of the adjacent polycrystalline silicon films 204 through a contact hall formed at the interlayer insulating film 205.

Pads 207 are provided as electrodes, and each of the pads 207 is arranged at the end portion of the wiring 206. A protection film 208 (e.g., nitride silicon film) is arranged to cover the wiring 206 except the pad 207. An infrared absorption film 209 is disposed on the protection film 208 corresponding to the forming field of the membrane 210, and covers at least a part of the thermocouple. In FIG. 8A, the forming field of the infrared absorption film 209 is indicated by alternate long and short dashed lines.

With reference to FIGS. 8A and 8B, the second detection unit 170 can be constructed of the semiconductor distortion gauges 220. The distortion gauges 220 are respectively arranged at the four sides of the membrane 210 having a substantial plan rectangle shape or the like, and form a conductive part to construct a PIEZO resistance near the end portion of the membrane 210. Pads 221 of the wirings are respectively connected with the distortion gauges 220.

Alternatively, the second detection unit 170 can be also constructed of a temperature sensor for detecting a temperature of the inner space 144 of the case member 140. In this case, the correction control unit corrects and controls the voltage applied to the Fabry-Perot filter 130 based on the detection signal of the temperature sensor.

More alternatively, in this case, the turning-on and turning-out of the light source 110 can be controlled. In this case, the first detection unit 120 outputs the detection signal corresponding to the infrared absorption amount during the period when the light source 110 comes on, and outputs the detection signal corresponding to the temperature of the inner space 144 during the period when the light source 110 is lights out. That is, in the construction shown in FIG. 6, the first detection unit 120 can also function as the temperature sensor for detecting the temperature of the inner space 144, without mentioning the pressure state of the inner space 144.

Figure 9:
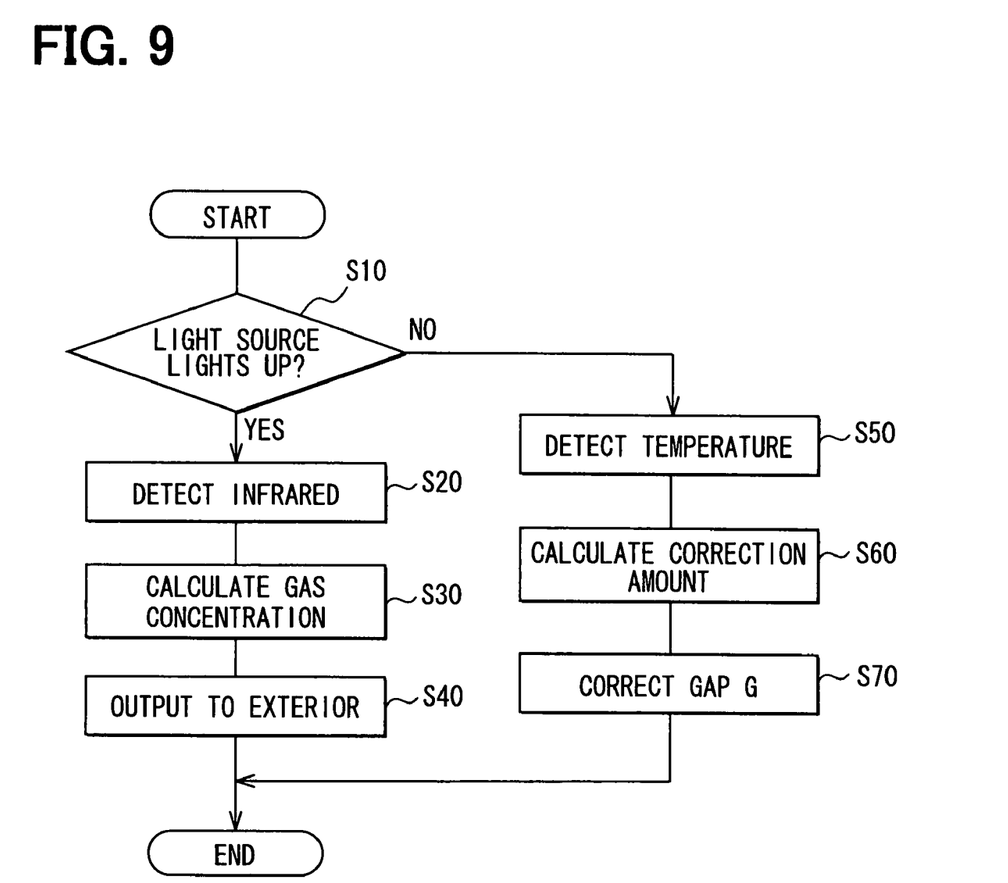
FIG. 9 is a flow chart showing a control operation of a control unit according to a second modification example of the third embodiment.

For example, according to a second modification example of this embodiment, in the case where the infrared-type gas detector 100 is mounted to a vehicle and the engine is actuated, the turning-on and turning-out of the light source 110 are switched at a predetermined timing by the control unit of the circuit chip 160. FIG. 9 shows a correction control operation of the control unit.

As shown in FIG. 9, at first, at step S10, it is determined whether or not the light source 110 lights up. In the case where it is determined that the light source 110 lights up, the first detection unit 120 detects the infrared at step S20. Thus, based on the detection signal of the first detection unit 120, the concentration of the detected gas is calculated at step S30 and the calculation result is outputted to the exterior at step S40. Thereafter, the control operation shown in FIG. 9 is ended.

On the other hand, in the case where it is determined that the light source 110 lights out, the temperature of the inner space 144 of the case member 140 is detected by the first detection unit 120 at step S50. Based on the detection signal of the first detection unit 120, the correction amount of the applied voltage based on the temperature variation is calculated at step S60, and the calculation result is outputted to the Fabry-Perot filter 130. At step S70, the gap G is corrected. Thereafter, the control operation shown in FIG. 9 is ended.

In this embodiment, the control operation from step S10 to step S70 shown in FIG. 9 is periodically repeated, for example.

The turning-on and turning-out of the light source 110 are periodically switched by the control unit of the circuit chip 160. Therefore, the infrared having the predetermined wavelength can pass through the Fabry-Perot filter 130 without being affected by the temperature variation, because the gap G of the Fabry-Perot filter 130 is periodically corrected. Thus, the detection sensitivity of the infrared-type gas detector 100 can be improved.

Moreover, according to the above-described construction, the infrared-type gas detector 100 can be small-sized as compared with the construction where the temperature sensor as the second detection unit is provided separately from the first detection unit.

However, the correction control method based on the detection result of the detection unit is not limited to the above-described example. For example, the correction control can be also performed in such a manner that the control unit changes the applied voltage, in the case where the detection result of the detection unit is larger than a predetermined value.

Moreover, in this embodiment, the inner space 144 can be also filled with filling gas having a lower viscosity than air, similarly to the second embodiment. In this case, the resistance of the filling gas when the moving mirror 136 has a displacement can decrease as compared with the pressure-reducing state by air. That is, the unevenness of the gap G of the Fabry-Perot filter 130 can be further reduced.

According to this embodiment, as shown in FIG. 7, the infrared-type gas detector 100 can have the light source 110, the first detection unit 120, the Fabry-Perot filter 130, the case member 140 and the housing 150. However, in addition to the construction where the turning-on and turning-out of the light source 110 are controlled (in this case, first detection unit 120 also function as temperature sensor), the infrared-type gas detector 100 can also include at least the first detection unit 120, the Fabry-Perot filter 130, and the case member 140 where the first detection unit 120 and the Fabry-Perot filter 130 are housed.

About the infrared-type gas detector 100, what has not described in the third embodiment is the same with the first embodiment.

OTHER EMBODIMENTS

Although the present invention has been fully described in connection with the preferred embodiments thereof with reference to the accompanying drawings, it is to be noted that various changes and modifications will become apparent to those skilled in the art.

For example, the circuit chip 160 can be arranged separately from the first detection unit 120. Alternatively, the circuits of the control units and the like constructed at the circuit chip 160 can be also arranged at the same board along with the first detection unit 120. In this case, the unevenness of the gap G of the Fabry-Perot filter 130 can be reduced, although the temperature of the case member 140 varies due to the generation of heat of the driving unit (for example, power transistor) constructing the circuit. Furthermore, the circuit chip 160 can be also constructed separately from the infrared-type gas detector 100.

Such changes and modifications are to be understood as being in the scope of the present invention as defined by the appended claims.

What is claimed is:

1. An infrared-type gas detector comprising:
a Fabry-Perot filter through which infrared having a predetermined wavelength is selected to pass;
a first detection unit for receiving the infrared having passed through the Fabry-Perot filter and outputting a detection signal corresponding to an absorption amount of the infrared; and
a case member having a window portion through which the infrared passes and housing therein the first detection unit and the Fabry-Perot filter in an inner space of the case member, wherein
the case member has at least one ventilation portion through which the inner space of the case member is communicated with the exterior of the case member.

2. The infrared-type gas detector according to claim 1, further comprising
a light source for radiating the infrared, wherein
the Fabry-Perot filter is arranged at a light path between the light source and the first detection unit.

3. The infrared-type gas detector according to claim 1, wherein
the case member has a plurality of the ventilation portions which are separated from each other.

4. The infrared-type gas detector according to claim 1, wherein
the case member has a pedestal portion where the first detection unit is mounted, and a cap portion which has the window portion and is assembled with the pedestal portion in such a manner that the first detection unit and the Fabry-Perot filter are housed in the cap portion.

5. The infrared-type gas detector according to claim 4, wherein
the ventilation portion is constructed of a through hole which is arranged at least one of the pedestal portion and the cap portion.

6. The infrared-type gas detector according to claim 5, wherein
at least one of the ventilation portions is arranged at a lower side than the Fabry-Perot filter in a vertical direction with respect to a ground surface.

7. The infrared-type gas detector according to claim 5, wherein
at least one of the ventilation portions is arranged at a top of the cap portion in a vertical direction with respect to a ground surface.

8. The infrared-type gas detector according to claim 4, wherein
the ventilation portion is constructed of a gap between a surface of the pedestal portion and that of the cap portion, the surfaces facing each other.

9. An infrared-type gas detector comprising:
a Fabry-Perot filter through which infrared having a predetermined wavelength is selected to pass;
a first detection unit for receiving the infrared having passed through the Fabry-Perot filter and outputting a detection signal corresponding to an absorption amount of the infrared; and
a case member having a window portion through which the infrared passes and defining therein an inner space which is substantially hermetically sealed and in which the first detection unit and the Fabry-Perot filter are housed, wherein
the inner space of the case member is in a pressure-reducing state as compared with an atmospheric pressure.

10. The infrared-type gas detector according to claim 9, wherein
the inner space of the case member is in a substantial vacuum state.

11. The infrared-type gas detector according to claim 9, wherein
the inner space of the case member is filled with a gas having a lower viscosity than air.

12. The infrared-type gas detector according to claim 9, further comprising
a light source for radiating the infrared, wherein
the Fabry-Perot filter is arranged at a light path between the light source and the first detection unit.

13. An infrared-type gas detector comprising:
a Fabry-Perot filter having a fixed mirror and a moving mirror which faces the fixed mirror and is spaced from the fixed mirror at a predetermined gap,
a predetermined voltage being applied between a fixed electrode arranged at the fixed mirror and a moving electrode arranged at the moving mirror to displace the moving mirror, so that the gap is changed and infrared having a predetermined wavelength corresponding the gap is selected to pass the Fabry-Perot filter;
a first detection unit for receiving the infrared having passed through the Fabry-Perot filter and outputting a detection signal corresponding to an absorption amount of the infrared;
a case member having a window portion through which the infrared passes and defining therein an inner space which is substantially hermetically sealed and in which the first detection unit and the Fabry-Perot filter are housed;
a second detection unit which is housed in the case member to detect at least one of a temperature and a pressure of the inner space of the case member; and
a control unit which corrects and controls the voltage applied between the fixed electrode and the moving electrode based on a detection result of the second detection unit.

14. The infrared-type gas detector according to claim 13, further comprising
a storage unit in which a corresponding relation among the applied voltage, at least one of the temperature and the pressure of the inner space, and the gap is beforehand memorized, wherein
the control unit controls the applied voltage based on the detection result of the second detection unit and the corresponding relation memorized in the storage unit.

15. The infrared-type gas detector according to claim 13, further comprising
a board where a membrane as a thin-walled portion is arranged, wherein:
the first detection unit is constructed of a light-receiving element and the second detection unit is constructed of a distortion gauge for detecting the pressure of the inner space; and
the light-receiving element and the distortion gauge are arranged at the same membrane.

16. The infrared-type gas detector according to claim 13, further comprising
a light source for radiating the infrared, wherein
the Fabry-Perot filter is arranged at a light path between the light source and the first detection unit.

17. The infrared-type gas detector according to claim 16, wherein:
the control unit controls a turning-on and a turning-out of the light source; and
the first detection unit outputs a detection signal corresponding to the infrared absorption amount during a period when the light source comes on, and outputs a detection signal corresponding to the temperature of the inner space during a period when the light source is lights out.

18. The infrared-type gas detector according to claim 13, wherein the inner space of the case member is filled with a gas having a lower viscosity than air.

19. The infrared-type gas detector according to claim 1, wherein the ventilation portion is covered by a dustproof filter which is breathing.

* * * * *